US011125761B2

(12) United States Patent
Bangert et al.

(10) Patent No.: US 11,125,761 B2
(45) Date of Patent: *Sep. 21, 2021

(54) METHODS AND DEVICES FOR RAPID ASSESSMENT OF SEVERITY OF INJURY

(71) Applicant: Antibodyshop A/S, Hellerup (DK)

(72) Inventors: Kristian Bangert, Holte (DK); Lars Otto Uttenthal, Salamanca (ES)

(73) Assignee: Antibodyshop A/S, Hellerup (DK)

( * ) Notice: Subject to any disclaimer, the term of this patent is extended or adjusted under 35 U.S.C. 154(b) by 327 days.

This patent is subject to a terminal disclaimer.

(21) Appl. No.: 15/889,311

(22) Filed: Feb. 6, 2018

(65) Prior Publication Data

US 2018/0172710 A1 Jun. 21, 2018

Related U.S. Application Data

(63) Continuation of application No. 14/802,023, filed on Jul. 17, 2015, now Pat. No. 9,927,446, which is a continuation of application No. 14/536,796, filed on Nov. 10, 2014, now abandoned, which is a continuation of application No. 12/302,931, filed as application No. PCT/DK2007/000254 on May 30, 2007, now abandoned.

(60) Provisional application No. 60/809,228, filed on May 30, 2006.

(51) Int. Cl.
*G01N 33/74* (2006.01)
*G01N 33/68* (2006.01)

(52) U.S. Cl.
CPC ......... *G01N 33/74* (2013.01); *G01N 33/6893* (2013.01); *G01N 2333/475* (2013.01); *G01N 2800/40* (2013.01); *G01N 2800/42* (2013.01); *G01N 2800/56* (2013.01)

(58) Field of Classification Search
CPC ........... G01N 2800/40; G01N 2800/42; G01N 33/74; G01N 33/6893; G01N 2333/475; G01N 2800/56
See application file for complete search history.

(56) References Cited

U.S. PATENT DOCUMENTS

| | | |
|---|---|---|
| 3,686,081 A | 1/1972 | Linzer et al. |
| 4,302,471 A | 11/1981 | Casagrande et al. |
| 4,357,343 A | 11/1982 | Madsen et al. |
| 4,376,110 A | 3/1983 | David et al. |
| 4,640,809 A | 2/1987 | Rumsdon et al. |
| 5,273,981 A | 12/1993 | Clark et al. |
| 5,405,832 A | 4/1995 | Potempa |
| 5,527,714 A | 6/1996 | Kosako |
| 5,552,313 A | 9/1996 | Calvet et al. |
| 5,627,034 A | 5/1997 | Gould et al. |
| 5,750,345 A | 5/1998 | Bowie |
| 5,939,272 A | 8/1999 | Buechler et al. |
| 6,136,526 A | 10/2000 | Venge |
| 6,143,720 A | 11/2000 | Conklin |
| 6,309,888 B1 | 10/2001 | Holvoet et al. |
| 6,447,989 B1 | 9/2002 | Comper |
| 6,498,142 B1 | 12/2002 | Sampath et al. |
| 6,537,802 B1 | 3/2003 | Alocilja et al. |
| 6,664,385 B1 | 12/2003 | Sanicola-Nadel et al. |
| 6,762,032 B1 | 7/2004 | Nelson et al. |
| 6,767,733 B1 * | 7/2004 | Green ..................... B01L 3/502 422/82.11 |
| 6,847,451 B2 | 1/2005 | Pugh |
| 6,986,995 B2 | 1/2006 | Rose et al. |
| 7,056,702 B2 | 6/2006 | Villanueva et al. |
| 7,153,660 B2 | 12/2006 | Moses et al. |
| 7,252,998 B2 | 8/2007 | Skerra et al. |
| 9,927,446 B2 * | 3/2018 | Bangert ................. G01N 33/74 |
| 2002/0048779 A1 | 4/2002 | Brady et al. |
| 2002/0110799 A1 | 8/2002 | Comper |
| 2003/0109420 A1 | 6/2003 | Validrs et al. |
| 2003/0119209 A1 | 6/2003 | Kaylor et al. |
| 2003/0175686 A1 | 9/2003 | Rose et al. |
| 2004/0121343 A1 | 6/2004 | Buechler et al. |
| 2004/0203083 A1 | 10/2004 | Buechler et al. |
| 2004/0219603 A1 | 11/2004 | Devarajan et al. |
| 2005/0261191 A1 | 11/2005 | Barasch et al. |
| 2005/0272101 A1 | 12/2005 | Devarajan et al. |
| 2006/0008804 A1 | 1/2006 | Chibout et al. |
| 2007/0037232 A1 | 2/2007 | Barasch et al. |
| 2007/0196876 A1 * | 8/2007 | Moses .............. G01N 33/57496 435/7.23 |
| 2007/0254370 A1 | 11/2007 | Devarajan et al. |

(Continued)

FOREIGN PATENT DOCUMENTS

| | | |
|---|---|---|
| EP | 1925877 | 5/2008 |
| WO | WO 95/029404 | 11/1995 |

(Continued)

OTHER PUBLICATIONS

Kunis et al. NGAL (Neutrophil Gelatinase-Associated Lipocalin) as a Marker for Tubular Damage in Patients with Acute Tubular Necrosis (ATN), Abstract SU-PO204, poster presentation at The American Society for Nephrology Renal Week 2004 (Oct. 27-Nov. 1, 2004 (Year: 2004).*
Bachorzewska-Gajewska et al. "Neutrophil gelatinase-associated lipocalin (NGAL) correlations with cystatin C, serum creatinine and eGFR in patients with normal serum creatinine undergoing coronary angiography", Nephrol Dial Transplant (2007) 22: 295-296, Sep. 2, 2006, doi: 10.1093/ndt/gfl408.*
Alessio et al. 1986. "Reliability of urinary creatinine as a parameter used to adjust values of urinary biological indicators" Int Arch Occup. Environ. Health 55: 99-106.
Allen RA, Erickson RW, Jesaitis AJ (1989): "Identification of a human neutrophil protein of Mr 24 000 that binds N-formyl peptides: co-sedimentation with specific granules". Biochim Biophys Acta 991: 123-133.

(Continued)

*Primary Examiner* — Christine Foster
(74) *Attorney, Agent, or Firm* — Suzannah K. Sundby, Esq.; Canady + Lortz LLP

(57) ABSTRACT

Methods and devices for rapid assessment of the severity of injury not due to a natural disease based upon measurement of neutrophil gelatinase-associated lipocalin (NGAL) are provided.

9 Claims, 1 Drawing Sheet

(56) References Cited

U.S. PATENT DOCUMENTS

| | | |
|---|---|---|
| 2008/0014604 A1 | 1/2008 | Devarajan et al. |
| 2008/0014644 A1 | 1/2008 | Barasch et al. |
| 2008/0090304 A1 | 4/2008 | Barasch et al. |
| 2009/0123941 A1 | 5/2009 | Devarajan et al. |
| 2009/0123946 A1 | 5/2009 | Birkenmeyer et al. |
| 2009/0123970 A1 | 5/2009 | Tu et al. |
| 2009/0124022 A1 | 5/2009 | Birkenmeyer et al. |
| 2009/0142774 A1 | 6/2009 | Devarajan et al. |
| 2009/0170143 A1 | 7/2009 | Uttenthal et al. |
| 2009/0181407 A1 | 7/2009 | Devarajan et al. |
| 2009/0197280 A1 | 8/2009 | Bangert |
| 2009/0269777 A1 | 10/2009 | Birkenmeyer |
| 2010/0015648 A1 | 1/2010 | Barasch et al. |
| 2012/0142022 A1 | 6/2012 | Tu |
| 2015/0064730 A1 | 5/2015 | Bangert |
| 2015/0323552 A1 | 11/2015 | Bangert |

FOREIGN PATENT DOCUMENTS

| | | | |
|---|---|---|---|
| WO | WO 96/32647 | 10/1996 | |
| WO | WO 2009/052392 | 4/2000 | |
| WO | WO 2009/052400 | 4/2000 | |
| WO | 200166140 A1 | 9/2001 | |
| WO | WO 01/066140 A1 * | 9/2001 | ........... A61K 39/395 |
| WO | WO 03/029462 | 4/2003 | |
| WO | WO 2003/029483 | 4/2003 | |
| WO | WO 2004/005544 | 1/2004 | |
| WO | WO 2004/088276 | 10/2004 | |
| WO | WO 2005/107793 | 11/2005 | |
| WO | WO 2005/121788 | 12/2005 | |
| WO | WO 2006/086587 | 6/2006 | |
| WO | WO 2007/044994 | 4/2007 | |
| WO | WO 2007098102 | 8/2007 | |
| WO | WO 2009/052390 | 4/2009 | |
| WO | WO 2009/059259 | 6/2009 | |
| WO | WO 2010/058378 | 6/2010 | |

OTHER PUBLICATIONS

Amin et al. "Identification of Putative Gene-Based Markers of Renal Toxicity" Environmental Health Perspectives; vol. 112, No. 4, Mar. 2004.
Anonymous (2007) Product inlay of the Quantikine Human MMP-9/NGAL Complex Immunoassay kit, Catalog No. DM9L20, R&D Systems. Inc., Minneapolis, MN, USA.
Antibodyshop O14a Product Specification ˙Antl-NGAL (human, neutrophil gelatinase-associated lipocalin) Mouse monoclonal antibody. Product No. HYB 211-01; Mar. 31, 2009.
Antioodyshop O14b Product Specification ˙Anti-NGAL (human, neutrophil gelatinase-associated lipocalin) Mouse monoclonal antibody, biolinylated. Product No. HYB 211-01 B; Mar. 31, 2009.
Antibodyshop O14c Product Specification ˙Anti-NGAL (human, neutrophil gelatinase-associated lipocalin) Mouse monoclonal antibody. Product No. HYB 211-02; Apr. 14, 2009.
Antibodyshop O14d Product Specification ˙Anti-NGAL (human, neutrophil gelatinase-associated lipocalin) Mouse monoclonal antibody, biotinylated. Product No. HYB 211-02 B; Apr. 14, 2009.
Antibodyshop O14e Product Specification ˙Anti-NGAL (human, neutrophil gelatinase-associated lipocalin) Mouse monoclonal antibody, Product No. HYB 211-05; Apr. 14, 2009.
Aulitzky et al., 1992, "Measurement of Urinary Clusterin as an Index of Nephrotoxicity", P.S.E.B.M, 1992, vol. 199, pp. 93-96.
Axelsson et al. 1995: "Studies of the release and turnover of a human neutrophil lipocalin". Scand J Clin Lab Invest, 55: 577-588.
Bachorzewska-Gajewska et al. (2006): "Neutrophil-gelatinase-asscciated lipocalin and renal function after percutaneous coronary interventions"; Am J Nephrol, vol. 26, pp. 287-292.
Baker M (2005); "In biomarkers we trust?": Nature Biotechnology, vol. 23, No. 3, pp. 297-304.
Balakumar et al. 2008. "Potential target sites to modulate vascular endothelial dysfunction: Current perspectives and future directions" Toxicology 245, 49-64.

Bangert et al. 2005. 'Urinary NGAL is dramatically increased in acute renal failure'. Abstract ESICM.
Bangert et al., Sep. 2006, "NGAL is significantly increased in urine and plasma in acute renal failure", Intensive Care Medicine, Spinger Verlag, BE, p. S10; XP009091902. (NGAL ITA study ESCIM 230906).
Bangert K. et al., Mar. 2007, "NGAL as a marker for renal injury in sepsis", Inflammation Research, Birkhauser Verlag, Basel, CH, pp. 104-105, XP008082913.
Barr et al. (2005): "Urinary creatinine concentrations in the U.S. Population: Implications for urinary biologic monitoring measurements"; Environmental Health Perspectives 113: 192-200.
Bartsch et al. "Cloning and expression of human neutrophil lipocalin cDNA derived from bone marrow and ovarian cancer cells" FEBS Lett. 357:255•239, 1995.
Bast et al. "Translational Crossroads for Biomarkers" Clin Cancer Res 2005; 11(I7). 6103-6108.
Bennett M et al (2008): "Urine NGAL predicts severity of acute kidney injury after cardiac surgery: A prospective study"; Clin J Am Soc Nephrol, vol. 3, pp. 865-873.
Bewick et al. 2004. "Statistics review 13: Receiver operating characteristic curves". Critical Care 0(6), 508-512.
Bläser et al. "A sandwich enzyme immunoassay for the determination of neutrophil lipocalin in body fluids". Clin Chim Acta 235 (1995); 137-145.
Bolignano D et al (2010): "Neutrophil gelatinase-associated lipocalin (NGAL) in human neoplasias: A new protein enters the scene"; Cancer Letters, vol. 288, No. 1, pp. 10-16.
Bolignano et al. 2007."Neutrophil Gelatinase-Associated Lipocalin in Patients with Autosomal-DominantPolycystic Kidney Disease". Am J Nephrol:27:373-378.
Bolignano et al. 2007. "Urinary Neutrophil Gelatinase-Associated Lipocalin (NGAL) is associated with severity of renal disease in proteinuric patients". Nephrol Dial Transplant; pp. 1-2.
Bolignano et al. 2008: "Neutrophil gets ease-associated lipocalin reflects the severity of renal impairment in subjects affected by chronic kidney disease"; Kidney Blood Press Res 31: 255-258.
Braunwald E et al (eds) (2002): "Harrison's Manual of Medicine"; McGraw-Hill Company; pp. 653.
Brenner & Rector (1986): The Kidney, 3rd edition, pp. 740-747.
Bu DX, Homdahl AL, Gabrielsen A, Fuxe J, Zhu C, Eriksson P, Yan ZQ (2006): "Induction of neutrophil gelatinase-associated lipocalin in vascular injury via activation of nuclear factor-kappaB", Am J Pathol 169:2245-2253.
Bungaard et al. 1994. "Molecular cloning and expression of a cDNA encoding NGAL: a lipocalin expressed in human neutrophils". Biochem Biophys Res Commun. Aug. 15; vol. 202(3):1468-75.
Carr MC et al (1994): "Urinary levels of the renal tubular enzyme N-acetyl-beta-D-glucosaminidase in unilateral obstructive uropathy"; The Journal of Urology; vol. 151, No. 2, pp. 442-445.
Chan et al. "The primary structure of rat alpha 2 mu globulin-related protein" Nucleic acid Res. vol. 16 No. 23 1988, pp. 11368.
Chertow et al (1997): "Preoperative Renal Risk Stratification"; Circulation, vol. 95, nr, 4, pp. 878-884.
Christensen El et al (2001): "Megalin and cubilin: synergistic endocytic receptors in renal proximal tubule"; Am J Physlol Renal Physiol, vol. 280, No. 4, pp. F562-F573.
CMS brochure; "Clinical Laboratory Improvement Amendments (CLIA)"; Department of Health and Human Services; Feb. 2004.
Cohen et al. 1993. "Induction of Type 2 Salivary Cystatin in Immunological and Chemical Kidney Injury" Critical Reviews in Oral Biology and Medicine, 4(3/4):553-563.
Costantini S et al (2002): "Pilot study on lipocalin expression into extracellular fluids of women in fertile age"; Minorva Ginecologica; vol. 64, No. 5, pp. 307-392.
Cowland et al. "Molecular Characterization and Pattern of Tissue Expression of the Gene for Neutrophil Gelatinase-Associates/ Lipocalin from Humans" Genomics 45: 17-23 1997.
Cruz DN et al (2009): "Plasma neutrophil gelatinase-associated lipocalin is an early biomarker for acute kidney injury in an adult ICU population"; Intensive Care Med., vol. 36, pp. 444-451; published online Dec. 3, 2009.

(56) References Cited

OTHER PUBLICATIONS

Dent et al. "Plasma neutrophil gelatinase-associated lipocalin predicts acute kidney injury, morbidity and mortality after pediatric cardiac surgery: a prospective uncontrolled cohort study" Crit Care 2007; 11(6):R127.

Devarajan et al. 2004. "NGAL: A novel early biomarker of renal injury following cardiac surgery". Slides, Cincinnati Children's Hospital Medical Center, University of Cincinatti, OH, Colombia University, NY.

Devarajen et al. 2006. "AACC Expert Access Program: Novel Diagnostic Markers of Early Acute Kidney Injury (AKI)". AACC, Online Dec. 14, 2006, pp. 1-45.

Devarajan. 2005, "Novel biomarkers for the early prediction of acute kidney injury". Cancer Therapy, vol. 3, 477-488.

Devireddy LR et al (2001): "Induction of Apoptosis by a Secreted Lipocalin That is Transcriptionally Regulated by IL-3 Deprivation"; Science, vol. 293, pp. 829-834.

Darnidharka VR et al (2002): "Serum crystatin C is superior to serum creatinine as a marker of kidney funciton: a meta-analysis", Am J Kidney Dis; vol. 40, No. 2; pp. 221-226.

Dorland's Illustrated medical dictionary, 29th Edition. W.B. Saunders Company, New York (2000): "cancer", "glomerulonephritis" and "neoplasm"; pp. 273, 752, 1184-1185.

Einelhoum et al. "Leukocyte activation detected by Increased plasma levels inflammatory mediators in patients with ischemic cerebrovascular diseases". Stroke 27:1734-1738, 1998.

E-mail correspondence—Trina Overgaard Østerbye, Jaya Mishra and Claus Morsø Schrøder, 2004.

EP 1831699 Opp1 Abbott; Jul. 2, 2010.
EP 1831699 Opp2 Getica; Aug. 3, 2010.
EP 1891699 Opp3 Alere; Aug. 11, 2010.
EP 1831699 Opp4 Phadia; Aug. 11, 2010.
EP 1831609 Reply to oppositions filed; Dec. 23, 2010.

Exhibit A of Dr. Kunis' declaration: cover page of onsite program/meeting brochure of the American Society of Nephrology Renal Week 2004, Oct. 27-Nov. 1, 2004, St. Louis Missouri.

Exhibit B of Dr. Kunis' declaration: p. 334 and 335 of the onsite program of the American Society of Nephrology Renal Week 2004, Oct. 27-Nov. 1, 2004, St. Louis Missouri, indicating poster presentation S-PO204 of Oct. 31, 2004.

Exhibit C of Dr. Kunis' declaration; photograph of the poster of Kunis et al., American Society of Nephrology Renal Week 2004, Oct. 27-Nov. 1, 2004, St. Louis Missouri, Ngal (neutrophil gelatinase-associated lipocalln) as a marker for tubular damage in patients with Acute Tubular Necrosis (ATM)'as presented during poster presentation SU-PO204.

Exhibit D of Dr. Kunis' declaration: clean copy reproduction/image file of the poster of Kunis et el., American Society of Nephrology Renal Week 2004, Oct. 27-Nov. 1, 2004, St Louis Missouri, "Ngal (neutrophil gelatinase-associated lipocalin) as a marker for tubular damage in patients with Acute Tubular Necrosis (ATN)" as presented during poster presentation SU-PO204.

Flower DR et al. (1991): "Mouse oncogene protein 24p3 is a member of the Lipocalin protein family; Biochemical and" Biophysical Research Communications, vol. 180. No. 1, pp. 69-74.

Forsblad et al. 2002 "Clinical manifestations of atherosclerosis in an elderly population are related to plasma neopterin, NGAL end endothelin-1, but not to Chlamydia pneumoniac serology". Int. Angiology 21(2) 173-9.

Fortescue EB et al (2000): "Predicting acute renal failure after coronary bypass surgery: cross-validation of two risk-stratification algorithms"; Kidney International; vol. 57, No. 6, pp. 2594-2602.

Fraser Chap 4 in Biological Variation: From Principles to Practice, AAAC Press, pp. 91-116, 2001.

Friedl et al. 1999. "Neutrophil gelatinase-assodated lipocalin in normal and neoplastic human :issue. Cell type-specific pattern of expression". The Histochemical Journal, 31, pp. 433-441.

Gale encyclopedia of medicine. "Definition of Blood plasma and serum in the Medical": www.freedictionary.com; accessed on Nov. 30, 2010.

Grenler et al. "Evaluation of the ARCHITECT urine NGAL assay: Assay performance, specimen handling requirements and biological variability" Clin Biochem. Apr. 2010; 43-615-650.

Han et al. 2002. "Kidney Injury Molecule-1 (KIM-1): A novel biomarker for human renal proximal tubule Injury". Kidney International, vol. 62. pp. 237-244.

Harbeson, A.E. 1936 "A case of turpentine poisoning" The Canadian Medical Association Journal, vol. 35, 549-550.

Henderson's Dictionary of Biological Terms, 12th edition, Prentice Hall; Blood and "Olooci serum"; pp. 74-77, 576-577.

Herget-Rosenthat (2005): "One step forward in the early detection of acute renal failure"; Lancet, vol. 365, No. 9466, pp. 1205-1206.

Hraba-Renevey S et al. (1989): "SV40-induced expression of mouse gene 24p3 involves a post-transcriptional mechanism"; Oncogene, vol. 4, No. 5, pp. 601-608.

Hrubec TC et al (2002): "Plasma versus serum: specific differences in biochemical analyte values": Journal of avian medicine and surgery; vol. 16, No. 2, pp. 101-105.

http://en.wikipedia.org/wiki/Diabetes_mellitus; "Diabetes Mellitus"; Wikipedia, The Free Encyclopedia; accessed on Feb. 10, 2011.

Hvidberg V et al (2005): "The endocylic receptor megalin binds the iron transporting neutrophil-gelatinase-associated lipocalin with high affinity and mediates its cellular uptake"; FEBS Letters, vol. 579, No. 3, pp. 773-777.

Haase M et al (2009): "Novel biomarkers early predict the severity of acute kidney injury after cardiac surgery in adults"; The Annals of thoracic surgery, vol. 88, No. 1, pp. 124-130.

Haase-Fielitz A et al (2009): "Novel and conventional serum biomarkers predicting acute kidney injury in adult cardiac surgery—a prospective cohort study"; Critical Care Medicine; vol. 37, No. 2, pp. 553-560.

Haase-Fielitz A et al (2009):"The predictive performance of plasma neutrophil gelatinase-associated lipocalin (NGAL) increases with grade of acute kidney injury"; Nephrol Dial Transplant, vol. 24, No. 11, pp. 3349-3364.

Ichimura T et al (1998): "Kidney injury molecule-1 (KIM-1), a putative epithelial cell adhesion molecule containing a novel immunoglobulin domain, is up-regulated in renal cells after injury"; Journal og Biological Chemistry, vol. 273, No. 7, pp. 4135-4142.

Jones AP et al (1996): "Urinary N-acetyl-B-glucosominidase activity in Type I diabetes mellitus"; Ann Clin Biochem; vol. 32, pp. 58-62.

Jönsson P et al (1999): "Extracorporeal circulation causes release of neutrophil gelatinase-associated lipocalin (NGAL)"; Mediators of Inflammation; vol. 8, No. 3, pp. 169-171.

Kieldsen et al. "Isolation and Characterization of Gelatinase Granules From Human Neutrophils" Blood, vol. 83, No. 6 (Mar. 15). 1994: pp. 1640-1649.

Kjeldsen L et al (1993): "Isolation and Primary Structure of NGAL, a Novel Protein Associated with Human Neutrophil Gelatinase"; J Biol. Chem.; vol. 268, No. 14, pp. 10425-10432.

Kjeldsen L et al (1993): "Structural and functional heterogeneity among peroxidase-negative granules in human neutrophils: identification of a distinct gelatinase-containing granule subset by combined immunocylochemistry and subcellular fractionation"; Blood, vol. 82, No. 10, pp. 3183-3191.

Kjeldsen L et al (1994): "Identification of neutrophll gelatinase-associated lipocalin as a novel matrix protein of specific granules in human neutrophils"; Blood, vol. 83, No. 3, pp. 799-807.

Kjeldsen L et al (2000):"Human neutrophil gelatinase-associated lipocalin and homologous proteins in rat and mouse"; Biochimica of Biophysics Acta, vol. 1482, No. 1-2, pp. 272-283.

Kjekisen L. et al., "Characterization of two ELISAs for NGAL, a newly described lipocalin in human neutrophils", J. of Immunological Methods, Elsevier Schience Publishers B.B., Amsterdam, NL, vol. 198, No. 2, Nov. 13, 1996, pp. 155-164.

Kotanko et el., 2000, "Urinary N-Acetyl-beta-D-Glucosaminidase and Neopterin Aid in the Diagnosis of Rejection and Acute Tubular Necrosis in Initially Nonfunctioning Kidney Grafts", Nephron 2000;84:228-235.

Kunis declaration and poster—Oct. 31, 2004. from Opposition proceedings against EP 1 831 699.

(56) References Cited

OTHER PUBLICATIONS

Kunls et al., Poster abstract 3709 published on Oct. 31, 2004. American Society of Nephrology Renal Week 2004.
LaBaer J (2005): "So, you want to look for biomarkers (Introduction to the special biomarkers issue)"; Journal of Proteome Research, vol. 4, No. 4, pp. 1053-1059.
Lim R et al (2007): "Neutrophil gelatinase-associated lipocalin (NGAL) art early-screening biomarker for ovarian cancer: NGAL is associated with epidermal growth factor-induced epithelia-mesenchymal transition"; Int. J. Cancer; vol. 120, No. 11, pp. 2426-2434.
Matthaeus et al. (2001); "Co-regulation of neutrophil geletinese-associated lipocalin and matrix metalloproteinase-9 in the post ischemic rat kidney"; J Am Soc Nephrol (2001); 12:787A.
Matthaeus T et al (2001): "Acute Ischemic Renal Failure Induces Expression of Neutrophil Gelatinase-Associated Lipocalin and Matrix Metalloproteinase-9 in Damaged Tubull"; Kidney and Blood Pressure Res., vol. 24, pp. 342 (Poster 268).
Mehta et al. 2007: "Acute kidney injury network: report of an initiative to improve outcomes in acute kidney injury". Critical Care 11(2), R31.
Mishra et al. 2004. "Neutrophil gelatinase-associated lipocalin: A novel early urinary biomarker for cisplatin nephrotoxicity". Am. J Nephr, 24: 307-315 (Published online on May 12, 2004).
Mishra J. et al, "Identification of neutrophil gelatinase-associated lipocallin as a novel early urinary biomarker for ischemic renal injury", Journal of the American Society of Nephrology, Williams and Wilkinds Baltimore, MD, US, vol. 14, No. 10, Oct. 1, 2003, pp. 2534-2543.
Mishra J. et al., Apr. 2, 2005, "Neutrophil gelatinase-associated lipocalin (NGAL) as a biomarker for acute renal injury after cardiac surgery", Lancet The, Lancet Limited. London GB, pp. 1231-1238, XP004824250.
Molitoris BA (2003), "Transitioning to therapy in ischemic acute renal failure", J.Am.Soc. Neuphrol 14: pp. 265-267.
Monier et al., 2000, "Geletine Isoforms in urine from bladder cancer patients", Clinica Chimica Acta 299 (2000) 11-23.
Moore RE (2005) "An historical perspective an the clinical diagnostic laboratory", In "Molecular Diagnostics for the Clinical Laboratorian" 2nd edition, edited by Coleman WB and Tsongalls GJ, published by Humana Press, NJ. pp. 4-5.
Mori et al. "Endocytic delivery of lipacalin-siderophore-iron complex rescues the kidney from injury ischemia-reperfusion injury" The Journal of Clinical Investigation; 115(3), 620-621, Mar. 2005—Enlarged and magnified version of Figure 1C, with logarithmic y-axis values and gridlines added.
Mori et al. 2006. "Endocylic delivery of lipocalin-siderophore-iron complex rescues the kidney from ischemia-reperfusion injury". The Journal of Clinical Investigation, vol. 115, No. 3, 610-621.
Mori K & Nakao K (2007):"Neutrophit gelatinase associated lipocalin as the real-time indicator of active kidney damage"; Kidney International, vol. 71, pp. 967-970.
Moses et al. 1998, "Increased Incidence of Matrix Metalloproteinases in Urine of Cancer Patients" Cancer Research, vol. 58, 1395-1399.
Muramatsu et al., 2002, "Early detection of cystein rich protein 61 (CYR61, CCN1) in urine following renal ischemic reperfusion injury", Kiney International, vol. 62 (2002) pp. 1601-1610.
Nickolas et al. 2008. "Sensitivity and Specificity of a Single Emergency Department Measurement of Urinary Neutrophil Gelatinase—Associated Lipocalin for Diagnosing Acute Kidney Injury". Annals of Internal Medicine, Jun. 3, 2008, vol. 148, No. 11, pp. 810-819.
Nielson et al. 1999. "Rectal dialysis and fecal concentrations of neutrophil gelatinase-associated lipocatin, interleukin-8, and tumor necrosis factor-alpha in ulcaractive colitis" The American Journal of Gastroenterology, 94:2923-2928.
Nykjaer A et al (1999): "An endocytic pathway essential for renal uptake and activation of the steroid 25-(OH) vitamin D3"; Cell, vol. 98, No. 4, pp. 607-615.
Ohlsson et al. 2003. "Increased circulating levels of proteinase 3 in patients with anti-neutrphilic cytoplasmic autoantibodies-assodated systemic vasculitis in remission". Clin Exp.Immunol, 131:528-535.
Parikh CR et al (2004): "Urinary interleukin-18 is a marker of human acute tubular necrosis"; Am J Kidney Dis; vol. 43, No. 3, pp. 405-414.
Parikh et al (2006): "Urine NGAL and IL-18 are predictive biomarkers for delayed graft function following kidney transplantation"; Am J Transplant, vol. 6, No. 7, pp. 1639-1645.
Parikh et al. 2005. "NGAL and IL-18: Novel early sequential predictive biomarkers of acute kidney injury after cardiac surgery", Abstract, contact view.
Pawlucyk Iza & Harris (1999): "A Role for a novel 24p3-like protein macrophage-mediated mesangial cell injury"; Abstract 59, Meeting of the Renal Association Apr. 22-23, 1999, Royal College of Physicans of Ireland, Dublin. Also published in Kidney International Meeting Abstracts, Blackwell Svoergy D9 and D16.
Pawlucyk Iza et al (2003): Macrophage-induced rat mesongial cell expression of the 24p3-like protein alpha-2-microglobulin-related protein; Biochimica et Biophysica Acta, vol. 1645, pp. 218-227.
Penders et al., 2004, "Alpha 1-microglobulin: clinical laboratory aspects and applications", Clinics Chimica Acta 346 (2004) 107-118.
R414 Request for stay of proceedings to EPO, Mar. 5, 2009. from Opposition proceedings against EP 1 831 699 B1.
R414DK00 Decision from Legal Division; Aug. 12, 2000. from Opposition proceedings against EP 1 831 699 B1.
R414DK00 EPO resumes proceedings; Jul. 10, 2009. from Opposition proceedings against EP 1 831 699 B1.
R414DK00 Letter with withdrawal; Sep. 25, 2009. from Opposition proceedings against EP 1 831 699 B1.
R414DK00 Third party does not appeal Sep. 28, 2009. from Opposition proceedings against EP 1 831 699 B1.
R414DK00 withdrawal DK; Sep. 23, 2009. from Opposition proceedings against EP 1 831 699 B1.
R414SK00 Withdrawal EN; Sep. 23, 2009. from Opposition proceedings against EP 1 831 699 B1.
Riordan et al. 2002. "Poisoning in children 4: Household products, plants, and mushrooms" Arch Dis Child 87: 403-406.
Rudd P.M. et al. (Oct. 1999), "Clyeosylation of natural human neutrophil gelatinase B. and neutrophil gelatinase B-associated lipocalin" Biochemistry Oct. 19, 1999 American Chemical Society US, vol. 38, No. 42, pp. 13937-13950.
Ryon et al (2002): "High expression in involuting reproductive tissues of uterocalin/24p3, a lipocalin and acute phase protein": Biochemical Journal, vol. 367, pt. 1, pp. 271 7.
Scherberich JE, Wiemer J, Schoeppe W (1992) "Biochemical and immunological properties of urinary angiotensinase A and dipeptidylaminopeptidase IV. Their use as markers in patients with renal cell injury". Eur J Clin Chem Clin Biochem 30:663-668.
Solberg. 1994. Textbook of Clin Chem. Chapt. 13 2nd ed. "Establishment and Use of Reference Values" pp. 454-484.
Sorof JM et al (1999): "Early initiation of peritoneal dialysis after surgical repair of congenital heart disease"; Pediatr Nephrol, vol. 13, No. 8, pp. 641-645.
Stoesz and Gould. 1995, "Overexpression of neu-related lipocalin (NRL) in neu-initiated but not ras or chemically initiated rat mammary carcinomas", Oncogene, 11, 2233-2241.
Suzuki M et al (2008): "Neutrophil gelatinase-associated lipocalin as a biomarker of disease activity in pediatric lupus nephritis"; Pediatric Nephrology, vol. 23, No. 3, pp. 403-412.
Tang S, Leung JC, Abe K, Chan KW, Chan LY, Chan TM, Lai KN (2003): "Albumin stimulates interleukin-B expression in proximal tubular epithelial cells in vitro and in vivo". J Clin Invest 111:515-527.
Thadhani et al. "Acute renal failure" NEJM, vol. 334, No. 22, pp. 1448-1460, 1996.
The defendant's amended version of EP 1831699; Jun. 18, 2008. Letter and amended claims, 3 pages.
The Merck Manual of patient symptoms—A concise pratical guide to etiology, evaluation and treatment; Eds, Robert S Porter, Justin L Kaplan, Barbara P. Homeler; Merck Research Laboratories, Whitehouse

(56) References Cited

OTHER PUBLICATIONS

Station, NJ USA, 2008; Online medical library: "Acute Renal Failure";(Longer list of causes of ARF). (8 pages).
The Merck Manual of patient symptoms—A concise practical guide to etiology, evaluation and treatment; Eds. Robert S Porter, Justin L. Kaplan, Barbara P. Homeier; Merck Research Laboratories, Whitehouse Station, NJ, USA, 2008; Online medical library: "Causes of acute interstitial nephritis";( List of causes of ATM) (one page).
The protocol on Jurisdiction and the recognition of Decisions in Respect of the Right to the Grant of a European Patent, Oct. 6, 1973.
Triebel et al., Dec. 1992, "A 25 kDA alpha2-microglobulin-related protein is a component of the 125 kDA form of human gelatinase", FEBS 11904, vol. 314, No. 3, pp. 386-388.
Tsuchida et al., 2003, "Lipocalin-Type Prostaglandin D Synthase in Urine in Adriamycin-Induced Nephropathy of Mice", Nephron Physiol, 2004; 96: p. 42-61.
Tuladhar et al. "Rapid Detection of Acute Kidney Injury by Plasma and Urinary Neutrophil gelatinase-associated Lipocalin After Cardiopulmonary Bypass" J Cardiovasc Pharmacol, vol. 53, No. 3, Mar. 2009, pp. 261-266.
Tuttle KR et al (2003): "Predictors of ARF after cardiac surgical procedures"; Am J Kidney Dis; vol. 41, No. 1, pp. 76-83.
Uttenthal. 2005. "NGAL: a marker molecule for the distressed kidney". CU Nov. (two pages).
Uttenthal. 2007. "NGAL: how useful is the new marker of kidney damage", Clinical Laboratory International. (www.cli-online.com).
Venge P et al (1994): "Soluble markers of allergic inflammation"; Allergy, vol. 49, No. 1, pp. 1-8.
Venge P, Carlson M, Fredens K, Garcia R (1990). "The 40 kD-protein. A new protein Isolated from the secondary granules of human neutrophils". Joint International Conference on Leukocyte Biology, abstract. J Leukocyte Biol 1(suppl.):28.
Wagener G et al (2006): "Association between Increases in Urinary Neutrophil Gelatinase—associated Lipocalin and Acute Renal Dysfunction after Adult Cardiac Surgery"; Anesthesiology, vol. 105, pp. 485-491.
Wheeler D. et al. "Serum neutrophil gelatinase-associated lipocalin (NGAL) as a marker of acute kidney injury in critically ill children with septic shock". Crit care Med 2008, vol. 36, No. 4.
Wu et al. 1998. "Analytical and clinical evaluation of new diagnostic tests for myocardial damage". Clinica Chimica Acta, 272, 11-21.
Xin C et al (2000): "Urine Neutrophil Gelatinase-Associated Lipocalin and Interleukin-18 Predict Acute Kidney Injury after Cardiac Surgery": Renal Failure, vol. 30, pp. 904-913.
Xu and Venge. "Lipocalins as biochemical markers of disease" Biochim Biophys Acta, vol. 1482, (2000); 298-307.
Xu et al. "Serum measurements of human neutrophil lipocalin (HNL) discriminate between acute bacterial and viral infections" Scand J Clin Lab Invest, (1995); 55:125-131.
Xu SY, Carlson M, Engstrom A, Garcia R, Peterson CG, Venge P (1994): "Purification and characterization of a human neutrophil lipocalin (HNL) from the secondary granules of human neutrophils", Scand J Clin Lab Invest 54:365-376.
Yan et al., 2001, "The high molecular weight urinary matrix metalloproteinase (MMP) activity is a complex of gelatinase BMMP-9 and neutrophil gelatinase-associated lipocalin (NGAL). Modulation of MMP-9 activity by NGAL", The Journal of Biological Chemistry, vol. 276, No. 40, pp. 37258-37265.
Yang CW et al (2001): "Pharmacological preconditioning with low-dose cyclosporine or FK506 reduces subsequent ischemia/reperfusion injury in rat kidney"; Transplantation, vol. 72, No. 11, pp. 1753-1759.
Yilmaz et al. 2009: "Early prediction of urinary tract infection with urinary neutrophil gelatinase-associatod lipocalin"; Pediatr Nephrol 24: 2387-2392.
Yndestad A et al (2009): "Increased systemic and myocardial expression of neutrophil gelatinase-associated lipocalin in clinical and experimental heart failure"; European Heart Journal. vol. 30, No. 10, pp. 1229-1236.

Zanardo G et al (1994): "Acute renal failure in the patient undergoing cardiac operation. Prevelence, mortality rate, and main risk factors"; Journal of thoracic and cardiovascular surgery; vol. 107, No. 6, pp. 1489-1496.
Zappitelli et al. 2007, "Urine neutrophil gelatinase-associated lipocalin in an early marker of acute kidney injury in critically ill children: a prospective cohort study"; Crit Care, vol. 11, pp. R84.
Zerega B et al (2000): "Expression of NRL/NGAL (neu-related lipocalin/neutrophil gelatinase-associated lipocalin) during mammalian embryonic development and in inflammation"; Eur J Cell Biol.; vol. 70, No. 3, pp. 165-172.
Zhao H, Ito A, Sakai N, Matsuzawa Y, Yamashita S, Nojima H (2006); "RECS1 Is a negative regulator of matrix metalloptoteinese-9 production and aged RECS1 knockout mice are prone to aortic dilation". Circ J 70:615-624.
Zhu T et al (2002): "Cyclosporine A protects against apoptosis in ischaemic/reperfused rat kidneys"; Clin exp pharmacol physiol; vol. 29, No. 9, pp. 852-854.
Zweig & Campbell. (1993): "Receiver-Operating Characteristic (ROC) Plots: A Fundamental Evaluation Tool in Clinical Medicine". Clin Chem 39/4, 561-577.
Eriksen BO et al (2003): "Prediction of acute renal failure after cardiac surgery: retrospective cross-validation of a clinical algorithm"; Nephrol Dial Transplant, vol. 18, No. 1, pp. 77-81.
Eineihoum et al., "Leukocyte Activation in Atherosclerosis: Correlation with Risk Factors." Atherosclerosis 131:79-84, 1997.
Ashkenazi et al., 2006, Prehospital Disaster Med., vol. 21, pp. 20-23.
Fukuda et al., Oct. 18, 2004, (XP-002448534, "Differential gene expression profiles of radioresistant oesophagael cancer cell lines established by continuous fractionated irradiation", British Journal of Cancer, vol. 91, No. 8, pp. 1543-1550.
Gebhard et al., Mar. 3, 2000., (XP-002448535), "Is interleukin 6 an early marker of injury severity following major trauma in humans", Archives of Surgery, vol. 135, No. 3, pp. 291-295.
Liu Q. et al, Sep. 22, 1995, (XP-002448530), "Identification of a new acute phase protein", Journal of Biological Chemistry, vol. 270, No. 36, pp. 22565-22570.
Möller et al., Mar. 1, 1998, (XP-002448531), "Cytokines and acute phase reactants during flare-up of contact allergy to gold", American Journal of Contact Dermatitis, vol. 9, No. 1, pp. 15-22.
Roudkenar et al., Jan. 1, 2007, "Oxidative stress induced lipocalin 2 gene expression: Addressings its expression under the harmful conditions", Journal of Radiation Research, vol. 48, No. 1, pp. 39-44.
Vemula et al., Jun. 1, 2004, (XP-002446533), "Expresion profiling analysis of the metabolic and inflammatory changes following burn injury in rats", vol. 18, No. 1, pp. 87-98.
Yanagisawa et al., Nov. 10, 2004, (XP-002448532), "Complementary DNA microarray analysis in acute lung injury included by lipopolysaccharide and diesel exhaust particles", vol. 229, No. 10, pp. 1081-1087.
Cal, Linjun et al.; "The Orijin of Multiple Molecular Forms in Urine of HNL/NGAL."; Clin J Am Soc Nephrol, vol. 5, 2010; pp. 2229-2235.
Haase, Michael et al.; "Accuracy of Neutrophil Gelatinase-Associated Lipocalin (NGAL) in Diagnosis and Prognosis in Acute Kidney Injury: A Systematic Review and Meta-analysis", Am J of Kidney Diseases, vol. 54, No. 6, Dec. 2009 pp. 1021-1024.
Mishra Jaya et al.; "Neutrophil gelatinase-associated lipocalin (NGAL) as a biomarker for acute renal injury after cardiac surgery"; The Lancet Articles, vol. 365, Apr. 2005; pp. 1231-1238.
U.S. National Library og Medicine, "Acute Kidney Injury", Host: Medical Subject Headings (MeSH), No. D058186 Dec. 31, 2011, Dec. 30, 2014 Available from: [http://www.ncbi.olm.oih.gov/mesh/2team=acute+kidney+injury].
Klausen et al., "On Mouse and Man: Beutrophil Gelalinese Associated Lipocalin is not Involved in Apoptosis or Acute Response," European Journal of Haematology, 2005, vol. 75, pp. 332-340.
BioPorto A/S Press Release, "A/S to Launch Analysis for Novel Marker of Acute Kidney Injury," Sep. 22, 2005, (English Translation), 1 page.

(56) References Cited

OTHER PUBLICATIONS

Product Insert for NGAL ELISA Kit #036, BioPorto Diagnosis A/S, p. 1-12, May 2010.
Product Insert for NGAL Rapid ELISA Kit: #037, BioPorto Diagnosis A/S, p. 1-84, May 2010.
Vivino et al., "Risk Factors for Acute Renal Failure in Trauma Patients," Intensive Care Med (1998) 24: pp. 808-814, also recognized that trauma patients are at risk of developing kidney injury.
De Geus et al. "Time of Injury Affects Urinary Biomarker Predictive Values for Acute Kidney Injury in Critically Ill, Non-Septic Patients," BMC Nephrology 2013, 14:273, pp. 1-7.
Betsuyaku et al., "Neutrophil Granule Proteins in Bronchoalveolar Lavage Fluid from Subjects with Subclinical Emphysema," Am. J. Respir. Crit. Care Med., 1999; 159 pp. 1985-1991.
Cincinnati Children's Hospital Medical Center, "Study Shows Promise in Identifying Kidney Failure," Press release with public release date of Mar. 31, 2005, retrieved from http://www.eurekalert.org/pub_releases/2005-03/cchm-ssp033005.php, two pages.
Azizova et al., "Multi-Organ Involvement and Failure in Selected Accident Cases with Acute Radiation Syndrome Observed at the Mayak Nuclear Facility," British Journal of Radiology Supplement 27 (2005), pp. 30-35.
Nally, J.V., "Acute renal failure in hospitalized patients" Cleve Clin J Med., Jul. 2002:69(7):569-74.
Uettwiller-Geiger et al., "Multicenter Evaluation of an Automated Assay for Troponin I" Clinical Chemistry 48:6 (2002), 869-876.

\* cited by examiner

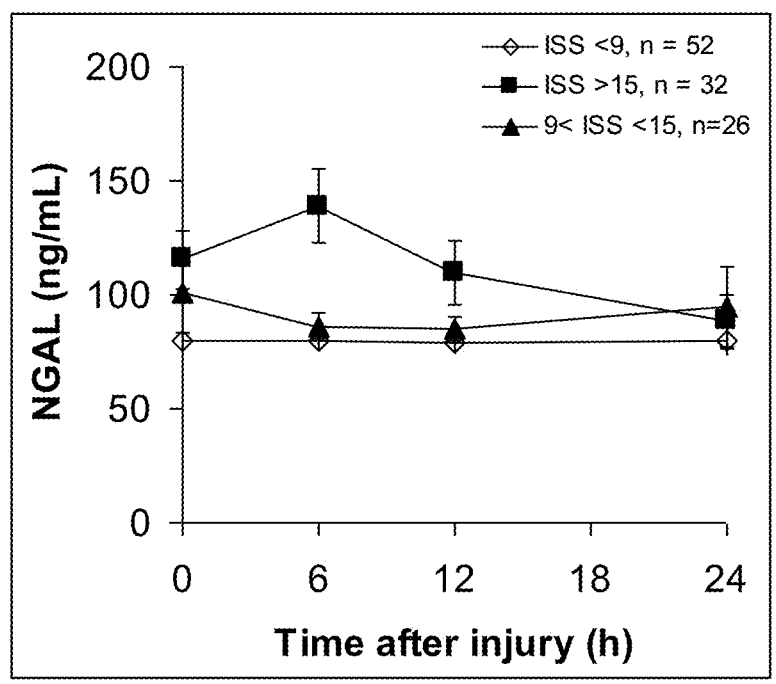

METHODS AND DEVICES FOR RAPID ASSESSMENT OF SEVERITY OF INJURY

CROSS REFERENCE TO RELATED APPLICATIONS

This application is a continuation of U.S. application Ser. No. 14/802,023, filed on Jul. 17, 2015, which is a continuation of U.S. application Ser. No. 14/536,796, filed on Nov. 10, 2014, which is a continuation of U.S. application Ser. No. 12/302,931, filed on Mar. 1, 2009, which is the U.S. national phase of PCT/DK2007/000254 filed on May 30, 2007, which claims the benefit of U.S. Provisional Application No. 60/809,228, filed on May 30, 2006, all of which are hereby incorporated by reference in their entireties.

FIELD OF THE INVENTION

The present invention provides methods and devices for assessing the severity of injury in a subject due to physical or chemical causes, ie not due to natural disease and prognosticating survival of the injured subject by measurement of a biomarker in a bodily fluid of the subject at the site of injury, point of first care or the hospital. In these methods and devices, the biomarker measured is neutrophil gelatinase-associated lipocalin (NGAL). The present invention is thus useful in the field of clinical medicine and surgery, in particular in the fields of traumatology, trauma surgery, emergency medicine, critical care medicine, first aid and rescue work.

BACKGROUND OF THE INVENTION

The current method of assessing the severity of injury is by visual inspection and clinical examination by the first responder at the site of presentation of the injured subject. This is a subjective evaluation conditioned by the level of medical or first-aid training of the responder, which may vary from complete lack of training or experience to a high level of training and experience in emergency medicine and rescue work. However, it is difficult even for trained physicians to make a precise evaluation of the severity of injury of victims of mass-casualty incidents (Ashkenazi et al. Prehospital Disaster Med. 2006 21:20-23).

In everyday cases of injury, the injured subject will be brought at the slightest suspicion of non-triviality to a hospital or trauma center. In mass casualty situations such as accidents, natural disasters and hostile acts such as bomb explosions where a large number of people, typically in excess of 10, are injured, this is not feasible because of lack of immediately available resources. Thus, triage, defined as prioritizing of the injured survivors for treatment or transport to treatment facilities in order to obtain the best overall outcome in terms of survival or the avoidance of permanent disability, is applied. The more accurate the triage, the higher the survival rate and the lower the number of complications leading to prolonged hospitalization or lifelong disability.

Injury severity scoring, as exemplified by the Injury Severity Score (ISS), which is standard practice at many centers for the treatment of trauma, is based on an anatomic examination. It estimates the severity of the most severe injury to each part of the body. The procedure takes time and does not take into account changes in the patient's physiological state including those due to internal bleeding, changes in fluid balance and activation of the blood clotting system. Furthermore, injury severity scoring systems do not take into account the progression of such changes during the time interval from the injury to the moment of scoring.

The present invention remedies defects of injury severity scoring by measuring the concentration in a bodily fluid of a biomarker that reflects the body's response to injury and hence reflects the change in the condition of the patient.

SUMMARY OF THE INVENTION

An aspect of the present invention relates to a method for assessing severity and determining prognosis of an injury due to physical or chemical causes in subject comprising determining a level of neutrophil gelatinase-associated lipocalin (NGAL) in a bodily fluid of the subject. The method of the present invention is preferably performed in the field at the site of injury or at the first point of care or on admission to the hospital.

Another aspect of the present invention relates to portable devices for measuring a level of neutrophil gelatinase-associated lipocalin (NGAL) in a bodily fluid of the subject suffering from an injury due to the said causes which can be used at or near a site of injury or first point of care to assess severity and prognosis of the injury in the subject.

For preferred application of the present invention, methods and devices used to measure NGAL must be performable by persons without laboratory training on small, portable, preferably pocket-sized and battery-powered devices under field conditions, and give results within a few minutes.

BRIEF DESCRIPTION OF THE DRAWING

FIG. 1 shows plasma levels of NGAL (mean±standard error of the mean) in 52 patients with mild trauma (ISS<9), 26 patients with moderate trauma (ISS 9-15) and 32 patients with severe trauma (ISS>15) immediately on hospital admission (time 0) and at 6, 12 and 24 hours thereafter.

DETAILED DESCRIPTION OF THE INVENTION

The present invention relates to methods and devices for determining the severity and prognosis of injury due to physical agents such as impact, crush, blast, burns or irradiation, or any type of exposure to noxious chemical agents, in a subject, preferably a mammal, more preferably a human, by measuring a level of neutrophil gelatinase-associated lipocalin (NGAL) in a bodily fluid including, but not limited to blood, plasma, serum, urine and bronchoalveolar lavage fluid, preferably blood or urine. The injury may be any type of externally caused injury, but not a naturally occurring disease. Measurement of NGAL can be performed using any method or device that is capable of determining NGAL levels in either a quantitative or a qualitative manner. The result of this measurement provides objective information about the pathophysiological responses to the injury. Further, repeated measurements provide information about the progress of the injured subject. This will enable the health care provider or first responder at the scene at which the injured subject is encountered to institute appropriate immediate measures, to prioritize the care of the subject in relation to other injured subjects at the scene of a major accident, disaster or hostile attack, and to inform the hospital or other care facility that is due to receive the injured subject. The objective information regarding the injured subject's status will help the health care providers select and provide appropriate treatment as well. The present invention can be used in any situation in which this assessment of the consequences of injury is wanted, whether or not hospital facilities are available.

NGAL (neutrophil gelatinase-associated lipocalin) is a protein of neutrophils and certain epithelial cells, including epithelial cells of the respiratory tract, the gastrointestinal tract and the genito-urinary tract. We have surprisingly observed in a series of human subjects (see Example 4) that major trauma gives rise to a release of NGAL into the blood. The cellular or tissue origin of this rise is unknown, but it takes place so early that it cannot be attributed to pathologies that have previously been described to release NGAL, such as inflammation and renal ischemic injury. The increase in the concentration of NGAL in the bodily fluids may be the result of increased NGAL release from many organs and tissues, such as muscles, soft tissue in general and bones, and does not necessarily indicate a specific injury to a single organ. Determination of levels of NGAL in bodily fluids such as blood or urine in accordance with the present invention therefore provides an overall indication of the severity of injury and constitutes a prognostic indicator of the outcome. In a preferred embodiment the invention does not relate to an isolated injury of kidneys or to injury of kidneys at all.

Methods of the present invention can also be used to assess the degree of exposure of a subject to whole body radiation after e.g. nuclear detonation. Subjects who are not visibly injured may still be injured by penetrating ionizing irradiation of major epithelial structures, such as the epithelia of the gastrointestinal tract and lungs. The response of these epithelia to radiation injury will be reflected by an increased release of NGAL into the blood. Thus quantification of NGAL in the blood of a subject can be used to assess the severity of whole body exposure to ionizing radiation and can be used to determine whether the subject should be treated with free-radical scavenging agents designed to protect the subject from the effects of radiation exposure. Such drugs are toxic and it is an advantage to restrict their application to subjects that can be shown to have been sufficiently exposed to justify their use.

Methods of the present invention can also be used to assess the consequences of exposure of the subject to chemical agents, such as noxious chemical agents, especially exposure by the inhalation of gases, powders or aerosols. These will provoke release of NGAL from the epithelium of the respiratory tract and may have further effects to release NGAL from other tissues if absorbed into the circulation.

Methods of the present invention can also be applied to injured mammals other than humans, such as production animals like cattle. The quantification of NGAL in blood from an injured animal can provide important information about the cost-effectiveness of treating the animal and aid in decisions on whether the animal should be treated or sacrificed.

An important feature of the present invention is that a sample of bodily fluid in which NGAL is to be measured is taken as soon as possible after a time of 15 minutes is estimated to have elapsed since the injury, and in any case within no more than 12 hours of the injury, such as within 6 hours of the injury, preferably within 2 hours of injury and most preferably within 1 hour after the time of injury.

In accordance therewith and with the use of this invention to assess casualties in the field, the level of NGAL in the sample is preferably measured by a rapid method that can be performed by personnel who are not trained in laboratory techniques and which can be used in the field at the scene of accidents, including multi-casualty accidents, disasters or hostile acts. In this context, the term "rapid" means within 10 minutes, more preferably within 5 minutes and even shorter times, such as 2 minutes. The method and any devices of the present invention thus fall within the category of clinical analyses known as "point-of-care" or "near-patient" testing. The present invention is not limited to any particular test method or format. However, in a preferred embodiment, means for measuring NGAL levels in accordance with the present invention fulfills the requirements of providing the test result within the stated time, uses only equipment that can readily be carried to the site of testing, and can be operated by personnel without specialized training beyond a short introduction.

NGAL in bodily fluids has been quantified previously by immunoblotting ("Western" blotting) and enzyme-linked immunosorbent assay (ELISA). These methods are relatively slow and require non-portable laboratory equipment operated by trained staff. These methods are therefore unsuited to the preferred application of the present invention.

NGAL in a sample can also be measured indirectly, by determining a functional activity of the NGAL, for example by its capacity to bind a natural or synthetic ligand, the concentration of which can also be measured by means of an antibody.

Thus, by the term "level" as used herein it is meant to include concentration of NGAL and/or functional activity of NGAL.

Devices of the present invention measure an individual sample, which is preferably urine or more preferably whole blood taken with a sampling device separate from, or incorporated with the device, and for blood samples coated with an anticoagulant. The sample is applied to an individual test cassette, which contains the antibodies and antibody conjugates in a precisely aliquoted and stabilized form necessary for the analysis of NGAL levels. Such antibodies and antibody conjugates may be bound to a solid phase, or dissolved in a solution containing preservatives and stabilizers, either case permitting a shelf life of at least 6 months at an average ambient temperature of 25 degrees centigrade. The test cassette also contains the support systems that allow the analytical process to proceed automatically once the sample is applied and the cassette inserted into a portable reading instrument carried separately or incorporated within the device itself. The test cassette is small enough to permit at least 10 such cassettes to be carried in a pocket and to fit into a pocket-sized reading instrument, for example the dimensions are smaller, and preferably much smaller, than maximum dimensions of 15 cm long, 5 cm wide and 2 cm deep, the total volume not exceeding 50 cubic centimeters. Each production batch of test cassettes is produced with a consistency such that the coefficient of variation of test results obtained with the same sample applied to different individual cassettes is less than 10%, preferably less than 5%. Said features distinguish the analytical methods and devices to be used in the present invention from the analytical methods previously used to measure NGAL.

The method of the present invention in one embodiment comprises the steps of measuring the concentration of NGAL in a sample of bodily fluid from the individual whose injury is to be assessed, and comparing the measured concentration with a selected cutoff value determined to exceed the concentration values found in healthy, uninjured individuals. The extent to which the measured NGAL concentration exceeds the cutoff level is indicative of the intensity of the pathophysiological response to injury and hence provides an indication of the severity of the injury.

The cutoff level for blood plasma below which the concentration NGAL cannot be indicative of injury severity because such a level can be found in healthy, uninjured individuals is preferably a level of 80 ng/mL or more, such a value between 80 ng/mL and 110 ng/mL, such as 85 ng/mL, or 90 ng/mL, or 95 ng/mL, or 100 ng/mL, or 105 ng/mL.

The cutoff level for urine below which the concentration NGAL cannot be indicative of injury severity because such a level can be found in healthy, uninjured individuals is preferably a level of 10 ng/mL or more, such a value between 10 ng/mL and 30 ng/mL, such as 15 ng/mL, or 20 ng/mL, or 25 ng/mL.

There are various clinical situations in which the rapid analysis of NGAL in accordance with the present invention may be applied.

One exemplary embodiment is in mass-casualty situations such as major accidents, e.g. train crashes, or natural disasters, e.g. earthquakes, or acts of war or terror, e.g. bomb explosions, where there is a need for the triage of a large number of victims. The rescue worker will carry capillary blood sampling devices, and the equipment necessary for field measurement of NGAL. The use of the invention will provide an objective assessment of injury severity which will complement the visual assessment and improve the accuracy of triage, especially in cases of internal injury.

Another exemplary embodiment is at accidents, such as traffic accidents, involving a smaller number of casualties. The invention will enable the first responders to obtain an objective assessment of injury severity which may influence the decision on where to take the injured (i.e. to which level of trauma center) and will improve the information that they can give to the receiving hospital on what to expect.

Another exemplary embodiment is in situations where hospitals and medically trained personnel are far away. This could be in Navy or civilian ships at sea, coastguard or other patrols, or hunters, mountaineers, prospectors or explorers in remote areas. The invention will objective injury assessment to the rescuer who has to take the decision whether or not to get the injured to hospital by helicopter or by making for the nearest harbor.

Another exemplary embodiment is in situations where an injured subject has been transported to a trauma center and the steps necessary to ensure immediate survival have been taken. Determination of the NGAL concentration in a bodily fluid, or the change in concentration from a previous determination, will provide objective information on the subject's status or progression that assist in further clinical decision-making.

Another exemplary embodiment is the assessment of whole body radiation exposure in subjects that have been exposed to penetrating ionizing irradiation without traumatic injury. The estimation of radiation injury to organs such as the gastrointestinal tract and lungs will assist in deciding whether or not to treat with relatively toxic radiation protection drugs.

Another exemplary embodiment is the assessment of an injury due to intoxication, including exposure to noxious chemical agents in the form of gases, powders or aerosols.

Another exemplary embodiment is the assessment of an injured animal to assist in deciding whether or not to treat the animal.

The following non-limiting examples are provided to illustrate how the analysis of NGAL in accordance with the present invention may be performed.

EXAMPLES

Example 1: Immunochromatographic or "Lateral Flow" Device

A lateral flow device comprised of a strip of porous nitrocellulose is coated near its distal end with a capture antibody, capable of binding only NGAL, applied as a transverse band. A further transverse band of antibody against antibodies of the species from which the detection antibody is derived is placed distally to the capture antibody band and serves as a control of strip function. The proximal end of the strip contains the detection antibody against NGAL adsorbed or linked to labeled polystyrene particles or particles of dye complex. This is overlaid by a filter that retains red blood cells in the sample. When an aliquot of urine or blood (taken with an anticoagulant-coated capillary dispenser) is applied to the proximal end of the strip, the labeled particles attached to detection antibody travel along the strip by capillary attraction. When reaching the band of capture antibody, only those particles which have bound NGAL in the sample will be retained, giving rise to a detectable band. Particles reaching the control band of antibody against the detection antibody will produce a detectable band whether or not any NGAL has been bound. The intensity of the labeled bands can be read by eye in the case of colored particles or by means of the appropriate detection device for the label used. A positive result is indicated by color development or the accumulation of label in both bands, while a negative result is indicated by color development or other label only in the control band. Failure of color development or other label in the control band indicates inadequate strip function. The sensitivity of the test can be regulated by adjusting the proportion of labeled particles coated with detection antibody. Batches of strips can be pre-calibrated and equipped with a calibration code that can be read by the detection device, so that a quantitative or semi-quantitative result can be read from the device. The device may be a battery-powered handheld device of dimensions that allow it to be carried in an appropriate jacket or leg pocket of a rescue worker's uniform. Many variations of the individual aspects of this lateral flow technology are possible, as known to those skilled in the art.

Example 2: Minicolumn Device

The minicolumn contains a frit made of compressed polyethylene particles allowing the passage of fluid and red cells. The frit is coated with capture antibody against NGAL. The minicolumn is incorporated into a device, which by means of automated liquid handling allows the fixed volume of urine or anticoagulated blood to be applied at a fixed flow rate and volume, followed by detection antibody against NGAL complexed with dye. After the passage of wash solution, the color intensity of the frit is read by light diffusion photometry. The batches of frits are pre-calibrated and the minicolumns equipped with a calibration code that can be read by the device, so that a quantitative result can be displayed by the instrument without the need for prior calibration with standards. This portable instrument can also be made suitable for field use.

Example 3: Turbidimetric Device

The fixed volume of anticoagulated sample is dispensed into a cassette containing a dilution of antibody against NGAL. The reaction of the antibody with the NGAL in the sample produces turbidity proportional to the NGAL concentration, which can be read by a small, portable battery-operated photometer. The intensity of the turbidity signal can be increased by conjugating the NGAL antibodies to polystyrene microspheres. This or similar intensification methods using antibody-coated microparticles will probably be necessary because of the low concentration range at which NGAL has to be measured. Many variations of the individual aspects of this turbidimetric technology are possible, as known to those skilled in the art.

Notwithstanding the above, it is evident that the principle of estimating the extent of injury by the measurement of NGAL in a bodily fluid can also be applied within hospitals, where the measurement can be performed in automated equipment in central laboratories. Performance of the test in hospitals also extends the possible application of the invention to samples of fluids that cannot be obtained outside hospitals, such as bronchoalveolar lavage fluid.

In the following example, plasma NGAL was measured in a series of trauma patients immediately on admission to hospital to obtain the closest simulation of the invention that could be made without the availability of a portable device for measurement of NGAL at the site of accident.

Example 4: Plasma Levels of NGAL in Trauma Patients on Hospital Admission and During the First 24 Hours Thereafter Blood samples were collected from a series of 110 unselected trauma patients immediately on admission to a level-1 trauma center and at 6, 12 and 24 hours thereafter. The median time from the occurrence of injury to admission was 45 minutes. The plasma samples were subsequently analyzed for their concentration of NGAL by means of a sandwich ELISA technique and the results related to the injury severity score (ISS) for each patient. An ISS below 9 was classified as mild trauma, an ISS from 9 to 15 inclusive as moderate trauma, and an ISS above 15 was classified as severe trauma. The time courses of the plasma NGAL levels (mean±standard error of the mean (SEM)) for patients with mild (n=52), moderate (n=26) and severe (n=32) are shown in FIG. 1. The results show that the plasma level of NGAL on admission is directly related to injury severity and that this relation persists from the earliest time that a blood sample could be obtained to at least six hours thereafter.

What is claimed is:

1. A method for diagnosing and treating radiation injury in a human subject who has been exposed to radiation likely to cause injury of the epithelium of the gastrointestinal tract and/or lungs, said method comprising the steps of
    (a) obtaining a bodily fluid sample, said bodily fluid sample is a blood, serum, urine, or bronchoalveolar lavage fluid sample, from the human subject within 12 hours after the human subject has been exposed to ionizing radiation;
    (b) measuring a level of neutrophil gelatinase-associated lipocalin (NGAL) in the bodily fluid sample by applying antibodies capable of binding to NGAL to the bodily fluid sample;
    (c) comparing the measured level of NGAL to a selected cutoff value;
    (d) diagnosing the human subject as having radiation injury of the epithelium of the gastrointestinal tract and/or lungs based on the measured level of NGAL exceeding the selected cutoff value, wherein the higher the level of NGAL in the bodily fluid sample, the more severely the epithelium is likely to be injured; and
    (e) administering an effective amount of a radiation protection drug to the human subject diagnosed with radiation injury wherein the radiation protection drug is a free-radical scavenging agent.

2. The method of claim 1, wherein the bodily fluid sample is a blood sample, a serum sample, or a urine sample.

3. The method of claim 1, wherein the bodily fluid sample is a bronchoalveolar lavage fluid sample.

4. The method of claim 1, wherein the measurement of NGAL gives rise to a quantitative or qualitative signal that is read by visual inspection or by means of a portable reading device that is carried to wherever an injured subject may be encountered.

5. The method of claim 1, wherein NGAL is measured by an automated method.

6. The method of claim 1, wherein the sample of bodily fluid is obtained within 6 hours after the subject has been exposed to the ionizing radiation.

7. The method of claim 1, wherein the sample of bodily fluid is obtained within 2 hours after the subject has been exposed to the ionizing radiation.

8. The method of claim 1, wherein the cutoff value is between 80 ng/ml and 110 ng/ml.

9. The method of claim 1, wherein the sample of bodily fluid is obtained within 1 hour after the subject has been exposed to the ionizing radiation.

* * * * *